(12) United States Patent
Quintero et al.

(10) Patent No.: US 10,792,024 B2
(45) Date of Patent: Oct. 6, 2020

(54) SCAFFOLDS WITH CHANNELS FOR JOINING LAYERS OF TISSUE AT DISCRETE POINTS

(71) Applicant: Ethicon, Inc., Somerville, NJ (US)

(72) Inventors: Julian Quintero, Flemington, NJ (US); Leo B. Kriksunov, Ithaca, NY (US); Robert J. Tannhauser, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 306 days.

(21) Appl. No.: 15/278,376

(22) Filed: Sep. 28, 2016

(65) Prior Publication Data

US 2018/0085103 A1 Mar. 29, 2018

(51) Int. Cl.
| | | |
|---|---|---|
| A61B 17/00 | (2006.01) | |
| A61L 24/06 | (2006.01) | |
| A61L 24/10 | (2006.01) | |
| A61L 24/00 | (2006.01) | |
| A61L 24/04 | (2006.01) | |

(52) U.S. Cl.
CPC ...... *A61B 17/00491* (2013.01); *A61L 24/001* (2013.01); *A61L 24/0042* (2013.01); *A61L 24/046* (2013.01); *A61L 24/06* (2013.01); *A61L 24/106* (2013.01); *A61B 2017/00004* (2013.01); *A61B 2017/00495* (2013.01)

(58) Field of Classification Search
CPC ........ A61B 17/00491; A61B 17/07292; A61B 17/08; A61B 17/085; A61B 2017/00495; A61B 2017/081
See application file for complete search history.

(56) References Cited

U.S. PATENT DOCUMENTS

| | | | |
|---|---|---|---|
| 167,162 | A | 8/1875 | French |
| 2,508,855 | A | 5/1950 | Brown |
| 2,721,858 | A | 10/1955 | Joyner et al. |
| 2,722,220 | A | 11/1955 | Mestrand |
| 2,807,262 | A | 9/1957 | Lew |
| 2,905,174 | A | 5/1959 | Smith |
| 3,254,111 | A | 5/1966 | Hawkins et al. |
| 3,402,716 | A | 9/1968 | Baxter |

(Continued)

FOREIGN PATENT DOCUMENTS

| | | |
|---|---|---|
| CA | 2262408 | 8/2000 |
| CN | 102755216 A | 10/2012 |

(Continued)

OTHER PUBLICATIONS

3M™ Steri-Strip Adhesive Closures Product Catalog Brochure, (2011) 4 pages.

(Continued)

*Primary Examiner* — Alexander J Orkin

(57) ABSTRACT

A scaffold for joining two layers of tissue, comprises a substantially flat and flexible body having a top surface, a bottom surface and sidewalls; at least one channel within the body starting at an injection port; a plurality of first passages on the top surface and a plurality of second passages on the bottom surface, said passages in fluid communication with the channel; a plurality of third passages penetrating the body from the top surface to the bottom surface, said plurality of third passages not in fluid communication with the channel.

18 Claims, 9 Drawing Sheets

(56) References Cited

U.S. PATENT DOCUMENTS

| | | | |
|---|---|---|---|
| 3,520,300 A * | 7/1970 | Flower Guiles, Jr. | A61M 1/008 433/91 |
| 3,731,683 A | 5/1973 | Zaffaroni | |
| 3,888,247 A | 6/1975 | Stenvall | |
| 3,940,362 A | 2/1976 | Overhults | |
| 3,983,878 A | 10/1976 | Kawchitch | |
| 3,995,641 A | 12/1976 | Kronenthal et al. | |
| 4,068,664 A * | 1/1978 | Sharp | A61M 1/008 433/91 |
| 4,080,348 A | 3/1978 | Korpman | |
| 4,126,130 A | 11/1978 | Cowden et al. | |
| 4,140,115 A | 2/1979 | Schonfeld | |
| 4,263,906 A | 4/1981 | Finley | |
| 4,313,865 A | 2/1982 | Teramoto et al. | |
| 4,340,043 A | 7/1982 | Seymour | |
| 4,364,876 A | 12/1982 | Kimura et al. | |
| 4,390,519 A | 6/1983 | Sawyer | |
| 4,460,369 A | 7/1984 | Seymour | |
| 4,560,723 A | 12/1985 | Millet et al. | |
| 4,584,355 A | 4/1986 | Blizzard et al. | |
| 4,585,836 A | 4/1986 | Homan et al. | |
| 4,591,622 A | 5/1986 | Blizzard et al. | |
| 4,612,230 A | 9/1986 | Liland et al. | |
| 4,614,183 A | 9/1986 | McCracken et al. | |
| 4,630,603 A | 12/1986 | Greenway | |
| 4,655,767 A | 4/1987 | Woodard et al. | |
| 4,671,266 A | 6/1987 | Lengyel et al. | |
| 4,720,513 A | 1/1988 | Kameyama et al. | |
| 4,733,659 A | 3/1988 | Edenbaum et al. | |
| 4,767,401 A | 8/1988 | Seiderman | |
| 4,793,887 A | 12/1988 | Card et al. | |
| 4,793,888 A | 12/1988 | Card et al. | |
| 4,795,435 A | 1/1989 | Steer et al. | |
| 4,852,571 A | 8/1989 | Gadsby et al. | |
| 4,867,747 A * | 9/1989 | Yarger | A61M 1/008 604/263 |
| 4,872,450 A | 10/1989 | Austad | |
| 4,950,282 A | 8/1990 | Beisang et al. | |
| 4,966,605 A | 10/1990 | Thieler | |
| 4,999,235 A | 3/1991 | Lunn et al. | |
| 5,035,687 A | 7/1991 | Sandbank | |
| 5,059,424 A | 10/1991 | Cartmell et al. | |
| 5,086,763 A | 2/1992 | Hathman | |
| 5,088,483 A | 2/1992 | Heinecke | |
| 5,106,362 A | 4/1992 | Gilman | |
| 5,125,907 A | 6/1992 | Philpott | |
| 5,164,444 A | 11/1992 | Bernard | |
| 5,173,302 A | 12/1992 | Holmblad et al. | |
| 5,232,958 A | 8/1993 | Mallya et al. | |
| 5,254,132 A | 10/1993 | Barley et al. | |
| 5,259,835 A | 11/1993 | Clark et al. | |
| 5,266,371 A | 11/1993 | Sugii et al. | |
| 5,308,313 A | 5/1994 | Karami et al. | |
| 5,328,687 A | 7/1994 | Leung et al. | |
| 5,336,209 A | 8/1994 | Porzilli | |
| 5,415,626 A | 5/1995 | Goodman et al. | |
| 5,429,592 A | 7/1995 | Jensen | |
| 5,445,597 A | 8/1995 | Clark et al. | |
| 5,449,340 A | 9/1995 | Tollini | |
| D363,126 S | 10/1995 | Dusek | |
| 5,456,660 A | 10/1995 | Reich et al. | |
| 5,476,440 A | 12/1995 | Edenbaum | |
| 5,486,547 A | 1/1996 | Matsuda et al. | |
| 5,571,079 A | 11/1996 | Bello et al. | |
| 5,575,997 A | 11/1996 | Leung et al. | |
| 5,582,834 A | 12/1996 | Leung et al. | |
| 5,599,858 A | 2/1997 | Buchanan et al. | |
| 5,620,702 A | 4/1997 | Podell et al. | |
| 5,623,011 A | 4/1997 | Bernard | |
| 5,624,669 A | 4/1997 | Leung et al. | |
| D382,343 S | 8/1997 | Wandell et al. | |
| 5,653,769 A | 8/1997 | Barley, Jr. et al. | |
| D383,211 S | 9/1997 | Dunshee et al. | |
| 5,662,599 A | 9/1997 | Reich et al. | |
| D387,169 S | 12/1997 | Dunshee et al. | |
| D389,244 S | 1/1998 | Dunshee et al. | |
| 5,705,551 A | 1/1998 | Sasaki et al. | |
| D391,639 S | 3/1998 | Dunshee et al. | |
| 5,749,895 A | 5/1998 | Sawyer et al. | |
| 5,762,955 A | 6/1998 | Smith | |
| 5,780,048 A | 7/1998 | Lee | |
| 5,782,788 A | 7/1998 | Widemire | |
| 5,823,983 A | 10/1998 | Rosofsky et al. | |
| 5,823,986 A | 10/1998 | Peterson | |
| D402,371 S | 12/1998 | Haynes et al. | |
| 5,876,745 A | 3/1999 | Muraoka et al. | |
| 5,902,443 A | 5/1999 | Kanakubo et al. | |
| 5,928,611 A | 7/1999 | Leung | |
| 5,931,800 A | 8/1999 | Rasmussen et al. | |
| 5,947,917 A | 9/1999 | Carté et al. | |
| 5,951,505 A | 9/1999 | Gilman et al. | |
| 5,998,694 A | 12/1999 | Jensen et al. | |
| D424,699 S | 5/2000 | Allen | |
| 6,093,465 A | 7/2000 | Gilchrist et al. | |
| 6,125,265 A | 9/2000 | Yamamoto et al. | |
| 6,140,548 A | 10/2000 | Hansen et al. | |
| 6,143,352 A | 11/2000 | Clark et al. | |
| 6,155,265 A | 12/2000 | Hammerslag | |
| 6,183,593 B1 | 2/2001 | Narang et al. | |
| 6,217,603 B1 | 4/2001 | Clark et al. | |
| 6,238,692 B1 | 5/2001 | Smith | |
| 6,245,960 B1 | 6/2001 | Eaton | |
| 6,284,941 B1 | 9/2001 | Cox et al. | |
| 6,310,166 B1 | 10/2001 | Hickey et al. | |
| 6,329,564 B1 | 12/2001 | Lebner | |
| 6,352,704 B1 | 3/2002 | Nicholson et al. | |
| 6,410,818 B1 | 6/2002 | Oyaski | |
| 6,439,789 B1 | 8/2002 | Balance et al. | |
| D463,564 S | 9/2002 | Siegwart et al. | |
| 6,455,064 B1 | 9/2002 | Narang et al. | |
| 6,479,725 B1 | 11/2002 | Brothers | |
| 6,482,431 B2 | 11/2002 | Smith | |
| 6,512,023 B1 | 1/2003 | Malofsky et al. | |
| D472,319 S | 3/2003 | Oltmann | |
| 6,559,350 B1 | 5/2003 | Tetreault et al. | |
| 6,579,469 B1 | 6/2003 | Nicholson et al. | |
| 6,582,713 B2 | 6/2003 | Newell et al. | |
| 6,589,269 B2 | 7/2003 | Zhu et al. | |
| 6,595,940 B1 | 7/2003 | D'Alessio et al. | |
| 6,596,917 B2 | 7/2003 | Oyaski | |
| 6,599,318 B1 | 7/2003 | Gabbay | |
| 6,620,846 B1 | 9/2003 | Jonn et al. | |
| 6,632,450 B1 | 10/2003 | Gregory | |
| 6,635,272 B2 | 10/2003 | Leaderman | |
| 6,652,559 B1 | 11/2003 | Tetreault et al. | |
| 6,667,051 B1 | 12/2003 | Gregory | |
| 6,712,839 B1 | 3/2004 | Lönne | |
| 6,787,682 B2 | 9/2004 | Gilman | |
| 6,837,027 B2 | 1/2005 | Hickey | |
| 6,942,683 B2 | 9/2005 | Dunshee | |
| D520,639 S | 5/2006 | Dodd et al. | |
| 7,044,982 B2 | 5/2006 | Milbocker | |
| 7,066,934 B2 | 6/2006 | Kirsch | |
| 7,122,712 B2 | 10/2006 | Lutri et al. | |
| 7,144,390 B1 * | 12/2006 | Hannigan | A61F 7/10 604/313 |
| 7,164,054 B2 | 1/2007 | Mori et al. | |
| D548,348 S | 8/2007 | Nash | |
| 7,252,837 B2 | 8/2007 | Guo et al. | |
| D562,461 S | 2/2008 | Nash et al. | |
| 7,371,400 B2 | 5/2008 | Borenstein et al. | |
| D574,962 S | 8/2008 | Atkins et al. | |
| D580,553 S | 11/2008 | Nash | |
| 7,457,667 B2 | 11/2008 | Skiba | |
| D582,561 S | 12/2008 | Sachi | |
| D584,415 S | 1/2009 | Sachi | |
| 7,576,257 B2 | 8/2009 | LaGreca, Sr. | |
| D611,156 S | 3/2010 | Dunshee | |
| 7,713,463 B1 | 5/2010 | Reah et al. | |
| D618,810 S | 6/2010 | Tanigawa et al. | |
| 7,943,811 B2 | 5/2011 | Da Silva Macedo, Jr. | |
| 7,981,136 B2 | 7/2011 | Weiser | |
| 7,982,087 B2 | 7/2011 | Greener et al. | |

(56) References Cited

U.S. PATENT DOCUMENTS

| | | | |
|---|---|---|---|
| D646,789 S | 10/2011 | Barth | |
| 8,343,606 B2 | 1/2013 | Marchitto et al. | |
| 8,353,966 B2 | 1/2013 | Day et al. | |
| D679,098 S | 4/2013 | Ogawa | |
| D679,402 S | 4/2013 | Conrad-Vlasak et al. | |
| D679,403 S | 4/2013 | Heinecke et al. | |
| D679,819 S | 4/2013 | Peron | |
| D679,820 S | 4/2013 | Peron | |
| 8,528,730 B2 | 9/2013 | Grossman | |
| D691,730 S | 10/2013 | Smith et al. | |
| D692,566 S | 10/2013 | Adoni | |
| D693,010 S | 11/2013 | Mosa et al. | |
| D694,892 S | 12/2013 | Chan et al. | |
| 8,603,053 B2 | 12/2013 | Riesinger | |
| D697,216 S | 1/2014 | Chan et al. | |
| 8,642,831 B2 | 2/2014 | Larsen et al. | |
| 8,663,171 B2 | 3/2014 | Tambourgi et al. | |
| D707,829 S | 6/2014 | Chan et al. | |
| D708,751 S | 7/2014 | Chan et al. | |
| 8,777,986 B2 | 7/2014 | Straehnz et al. | |
| D712,045 S | 8/2014 | Thornton | |
| D713,967 S | 9/2014 | Adoni | |
| 8,884,094 B2 | 11/2014 | Lockwood et al. | |
| 9,000,251 B2 | 4/2015 | Murphy et al. | |
| RE45,510 E | 5/2015 | Hisamitsu | |
| D728,803 S | 5/2015 | Sinda et al. | |
| D745,688 S | 12/2015 | Chan et al. | |
| D745,689 S | 12/2015 | Chan et al. | |
| D746,479 S | 12/2015 | Arefieg | |
| D750,789 S | 3/2016 | Mackay et al. | |
| D757,950 S | 5/2016 | Karlsson et al. | |
| 9,339,417 B2 | 5/2016 | Ogawa | |
| 9,381,284 B2 | 7/2016 | Cornet et al. | |
| 9,492,171 B2 | 11/2016 | Patenaude | |
| 9,623,142 B2 | 4/2017 | Jonn et al. | |
| 9,655,622 B2 | 5/2017 | Jonn et al. | |
| 2001/0002432 A1* | 5/2001 | Bugge | A61M 1/008 604/28 |
| 2001/0028943 A1 | 10/2001 | Mashiko et al. | |
| 2001/0037077 A1 | 11/2001 | Wiemken | |
| 2002/0019652 A1 | 2/2002 | DaSilva et al. | |
| 2002/0037310 A1 | 3/2002 | Jonn et al. | |
| 2002/0185396 A1 | 12/2002 | Mainwaring et al. | |
| 2002/0192107 A1 | 12/2002 | Hickey | |
| 2002/0193721 A1 | 12/2002 | VanDruff | |
| 2003/0031499 A1 | 2/2003 | Heard et al. | |
| 2003/0093024 A1 | 5/2003 | Falleiros et al. | |
| 2003/0100955 A1 | 5/2003 | Greenawalt et al. | |
| 2003/0109819 A1 | 6/2003 | Tsuruda et al. | |
| 2003/0125654 A1 | 7/2003 | Malik | |
| 2003/0175824 A1* | 9/2003 | Pishko | B01L 3/5085 506/7 |
| 2003/0225355 A1 | 12/2003 | Butler | |
| 2004/0001879 A1 | 1/2004 | Guo et al. | |
| 2004/0060867 A1 | 4/2004 | Kriksunov et al. | |
| 2004/0120849 A1 | 6/2004 | Stewart et al. | |
| 2004/0142041 A1 | 7/2004 | MacDonald et al. | |
| 2004/0162512 A1 | 8/2004 | Liedtke et al. | |
| 2004/0220505 A1 | 11/2004 | Worthley | |
| 2005/0015036 A1 | 1/2005 | Lutri et al. | |
| 2005/0043820 A1* | 2/2005 | Browning | A61F 2/0077 623/23.74 |
| 2005/0085757 A1 | 4/2005 | Santanello | |
| 2005/0147457 A1 | 7/2005 | Badejo et al. | |
| 2005/0153090 A1 | 7/2005 | Marchitto et al. | |
| 2005/0154340 A1 | 7/2005 | Schlussel | |
| 2005/0208100 A1 | 9/2005 | Weber et al. | |
| 2005/0288706 A1* | 12/2005 | Widomski | A61B 17/0057 606/213 |
| 2006/0058721 A1 | 3/2006 | Lebner et al. | |
| 2006/0141012 A1 | 6/2006 | Gingras | |
| 2006/0173394 A1* | 8/2006 | Stroock | A61F 2/30756 602/41 |
| 2006/0265005 A1 | 11/2006 | Beese | |
| 2007/0106195 A1 | 5/2007 | Marcoux et al. | |
| 2007/0218101 A1* | 9/2007 | Johnson | A61B 17/88 424/423 |
| 2007/0272211 A1 | 11/2007 | Kassner | |
| 2007/0299542 A1 | 12/2007 | Mathisen et al. | |
| 2008/0051687 A1 | 2/2008 | Rogers | |
| 2008/0154168 A1 | 2/2008 | Lutri | |
| 2008/0086113 A1 | 4/2008 | Tenney et al. | |
| 2008/0109034 A1 | 5/2008 | Mather et al. | |
| 2008/0110961 A1 | 5/2008 | Voegele et al. | |
| 2008/0167633 A1 | 7/2008 | Vannucci | |
| 2008/0280037 A1 | 11/2008 | Sheridan et al. | |
| 2008/0302487 A1 | 12/2008 | Goodman et al. | |
| 2010/0106120 A1 | 4/2010 | Holm | |
| 2010/0262091 A1* | 10/2010 | Larsson | A61F 13/00068 604/304 |
| 2010/0298791 A1 | 11/2010 | Jones et al. | |
| 2011/0047766 A1 | 3/2011 | McAulay et al. | |
| 2011/0071415 A1* | 3/2011 | Karwoski | A61B 5/08 600/529 |
| 2011/0092874 A1 | 4/2011 | Baschnagel | |
| 2011/0208102 A1 | 8/2011 | Chawki | |
| 2011/0253303 A1 | 10/2011 | Miyachi et al. | |
| 2012/0220912 A1 | 8/2012 | Shang | |
| 2012/0238933 A1 | 9/2012 | Murphy et al. | |
| 2012/0277645 A1 | 11/2012 | Kikuta et al. | |
| 2013/0012988 A1 | 1/2013 | Blume et al. | |
| 2013/0041337 A1 | 2/2013 | Aali et al. | |
| 2013/0066365 A1 | 3/2013 | Belson et al. | |
| 2013/0084323 A1 | 4/2013 | Riebman et al. | |
| 2013/0138068 A1 | 5/2013 | Hu et al. | |
| 2013/0143326 A1 | 6/2013 | Tai et al. | |
| 2013/0144399 A1 | 6/2013 | Tai et al. | |
| 2013/0204077 A1 | 8/2013 | Nagale et al. | |
| 2013/0218125 A1 | 8/2013 | Stopek et al. | |
| 2013/0245784 A1 | 9/2013 | Tan et al. | |
| 2013/0274717 A1* | 10/2013 | Dunn | A61M 27/00 604/541 |
| 2013/0282049 A1 | 10/2013 | Peterson et al. | |
| 2013/0317935 A1 | 11/2013 | Ha et al. | |
| 2014/0024989 A1 | 1/2014 | Ueda | |
| 2014/0107561 A1 | 4/2014 | Dorian et al. | |
| 2014/0121649 A1 | 5/2014 | Calco | |
| 2014/0155916 A1 | 6/2014 | Hodgkinson et al. | |
| 2014/0171888 A1 | 6/2014 | Croizat et al. | |
| 2014/0257348 A1 | 9/2014 | Priewe et al. | |
| 2014/0257517 A1 | 9/2014 | Deichmann et al. | |
| 2015/0057491 A1 | 2/2015 | Goddard et al. | |
| 2015/0209186 A1 | 7/2015 | Abbott et al. | |
| 2015/0257938 A1 | 9/2015 | Pensier | |
| 2015/0314114 A1 | 11/2015 | La Rosa | |
| 2015/0351767 A1 | 12/2015 | Zoll et al. | |
| 2016/0030248 A1 | 2/2016 | Potters | |
| 2016/0089145 A1 | 3/2016 | Quintero et al. | |
| 2016/0296673 A1 | 10/2016 | Sambusseti | |
| 2017/0056568 A1 | 3/2017 | Shelton, IV et al. | |
| 2017/0056569 A1 | 3/2017 | Vendely et al. | |
| 2017/0189159 A1 | 7/2017 | Bartee et al. | |
| 2017/0273837 A1 | 9/2017 | Brueckner | |
| 2017/0367806 A1 | 12/2017 | Gingras et al. | |
| 2018/0085103 A1 | 3/2018 | Quintero et al. | |
| 2018/0085259 A1 | 3/2018 | Quintero | |
| 2018/0085260 A1 | 3/2018 | Quintero | |

FOREIGN PATENT DOCUMENTS

| | | |
|---|---|---|
| CN | 203234898 | 10/2013 |
| EP | 0532275 | 3/1993 |
| EP | 0730874 | 9/1996 |
| EP | 1161212 | 8/2000 |
| EP | 2359782 | 8/2011 |
| EP | 2377498 | 10/2011 |
| EP | 2805698 | 11/2014 |
| GB | 2078763 | 1/1982 |
| JP | 61-203020 | 12/1986 |
| JP | 62-87624 | 6/1987 |
| JP | 01-265967 | 10/1988 |
| JP | 2-140948 | 11/1990 |

(56) References Cited

FOREIGN PATENT DOCUMENTS

| | | |
|---|---|---|
| JP | 7-016258 | 1/1995 |
| JP | 2001-265967 | 9/2001 |
| JP | 2002-537068 | 11/2002 |
| JP | 2003-153949 | 5/2003 |
| JP | 2006-061263 | 3/2006 |
| JP | 2009-022730 | 2/2009 |
| JP | 1359502 S | 5/2009 |
| JP | 2011-004850 | 1/2011 |
| JP | 1571238 S | 3/2017 |
| WO | WO 1983/002586 | 8/1983 |
| WO | WO 1995/004511 | 2/1995 |
| WO | WO 1996/040797 | 12/1996 |
| WO | WO 1998/026719 | 6/1998 |
| WO | WO 2000/049983 | 8/2000 |
| WO | WO 2004/049987 | 6/2004 |
| WO | WO 2005/051259 | 6/2005 |
| WO | WO 2005/079674 | 9/2005 |
| WO | WO 2006/017109 | 2/2006 |
| WO | WO 2008/082444 | 7/2008 |
| WO | WO 2009/067062 | 5/2009 |
| WO | WO 2010/134873 | 11/2010 |
| WO | WO 2013/009725 | 1/2013 |
| WO | WO 2014/083570 | 6/2014 |
| WO | WO 2014/195710 | 12/2014 |
| WO | WO 2015/135351 | 9/2015 |

OTHER PUBLICATIONS

3M™ Steri-Strip Adhesive Closures Product Catalog Brochure, (2011) 8 pages.
3M™ Steri-Strip Adhesive Closures Product Catalog Brochure, (2012) 12 pages.
Allen, L.V. Jr et al Ansel's Pharmaceutical Dosage Forms and Drug Delivery Systems, 8th edition 2005 Lippincott Williams & Wilkins, Chapter 4, Dosage Form Design: Pharmaceutical and Formulation Considerations p. 131.
Ashley et al.: Further studies involving wound closure with a rapidly polymerizing adhesive; *Plastic and Reconstructive Surgery*; Apr. 1963; vol. 31; pp. 333-343.
Ashley et al.: Nonsutured closure of skin lacerations and nonsutured grafting of skin with a rapidly polymerizing adhesive; *Qtrly Bull. Northwestern University (Evanston, Ill.) Medical School*; 1962; vol. 36; pp. 189-194.
Brombeg et al.: Nonsuture fixation of split-thickness skin grafts; *Surgery*, Jun. 1964; vol. 55; pp. 846-853.
Cramer: Rapid Skin Grafting in Small Animals; *Plastic and Reconstructive Surgery and the Transplantation Bull*; Oct. 1962, vol. 30; pp. 149-150.
Cramer et al.: Autograft rejection induced by homografting. A phenomenon intermediate between homograft rejection and autoimmunity; *Plastic and Reconstructive Surgery*; Jun. 1965; vol. 35; pp. 572-587.
DeMaria, E. 'New skin closure system facilitates wound healing after cardiovascular implantable electronic device surgery' World Journal of Clinical Cases (2015) 3(8) pp. 675-677.
Dermabond Prineo Skin Closure Systems (22 cm) Brochure (2014), 7 pages.
Dermabond Prineo Skin Closure Systems (22 cm) Brochure (2015), 2 pages.
Healthcare Packaging. Advanced Wound Care Products and packaging Needs. Jun. 5, 2017 (earliest online date), [site visited May 8, 2018]. Available from the Internet, URL:https://www.healthcarepackaging.com/article/applications/healthcare/advanced-wound-care-products-and-packaging-needs> (Year: 2017).
Inou: Studies on the Surgical Use of Plastic Adhesive; *Am. Journal of Proctology*; 1962; vol. 13; pp. 219-226.
Jesse et al.: Fixation of split-thickness skin grafts with adhesive; *Plastic and Reconstructive Surgery*; Mar. 1964; vol. 33; pp. 272-277.

Kaplan: A technique of nonsuture wound closure with a plastic tissue adhesive; *Plastic and Reconstructive Surgery*; Feb. 1966; vol. 37(2); pp. 139-142.
Keddie et al.: Intrafollicular tinea versicolor demonstrated on monomer plastic strips; *Journal of Investigative Dermatology*; Sep. 1963; vol. 41; pp. 103-106.
Lazar, H.L. et al 'Novel Adhesive Skin Closures Improve Wound Healing Following Saphenous Vein Harvesting' J. Card Surg (2008) 23 pp. 152-155.
Leukosan SkinLink Application Guide (2006) 1 page.
Leukosan Skinlink. BSN Medical (2017) 1 page http://www.bsnmedical.com/products/wound%E2%80%90care%E2%80%90vascular/category%E2%80%90product%E2%80%90search/acute%E2%80%90wound%E2%80%90care/wound%E2%80%90closure/leukosanr%E2%80%90skinlink.html.
Pam Marketing Nut. Yikes! The Social Medica Quick Fix Band-Aids are Falling Off! Jul. 2012 [earliest online date], [site visited May 8, 2018]. Available from Internet, ,URL:http://www.pammarketingnut.com/2012/07/yikes-the-social-media-quick-fix-band-aids-are-falling-off/> (Year: 2012).
Parrish et al.: Synthetic resin adhesive for placement of skin grafts; *American Surgeon*; Nov. 1964; vol. 30; pp. 753-755.
Raekallio et al.: Acute reaction to arterial adhesive in healing skin wounds; *Journal of Surgical Research*; Mar. 1964; vol. 4; pp. 124-127.
Stone: Nonsuture closure of cutaneous lacerations, skin grafting and bowel anastomosis; *American Surgeon*; Mar. 1964; vol. 30; pp. 177-181.
Topaz, M. et al 'The TopClosure 3S System, for skin stretching and a secure wound closure' Eur Plast Surg (2012) 35 pp. 533-543.
TopClosure 3S System—Skin Stretching and Secure Wound Closure System Product Information Sheet (2010) 15 pages.
Wolfe et al.: The application of hydrostatic pressure to the burn injury, an experimental study: *Journal of Trauma: Injury Infections & critical Care*; May 1962; vol. 2; pp. 262-272.
ZipLine medical Zip Surgical Skin Closure Brochure (2013) 4 pages.
Communication received from the USPTO for co-pending U.S. Appl. No. 10/887,884 dated Aug. 11, 2006.
Communication received from USPTO for co-pending U.S. Appl. No. 10/779,721 dated Mar. 28, 2007.
Communication received from USPTO for co-pending U.S. Appl. No. 10/779,721 dated Apr. 16, 2007.
Communication received from the USPTO for co-pending U.S. Appl. No. 10/887,884 dated Mar. 6, 2008.
Communication received from the USPTO for co-pending U.S. Appl. No. 10/887,884 dated Dec. 12, 2008.
Communication received from the USPTO for co-pending U.S. Appl. No. 12/207,984 dated May 11, 2011.
Communication received from the USPTO for co-pending U.S. Appl. No. 12/163,021 dated May 13, 2011.
Communication received from the USPTO for co-pending U.S. Appl. No. 12/163,021 dated Feb. 2, 2012.
Communication received from the USPTO for co-pending U.S. Appl. No. 12/163,021 dated Jun. 22, 2012.
Communication received from the USPTO for co-pending U.S. Appl. No. 12/207,984 dated Jun. 28, 2012.
Communication received from USPTO for co-pending U.S. Appl. No. 12/163,021 dated Jun. 22, 2012.
Corrected International Search Report International Application No. PCT/US2005/004948 dated Jun. 22, 2005.
Extended European Search Report re: 14166813.7 dated Jul. 7, 2014.
In re the U.S. Appl. No. 12/163,021 the Non-Final rejection dated Aug. 14, 2013.
In re the U.S. Appl. No. 12/163,021 the Final rejection dated Jan. 3, 2014.
In re the U.S. Appl. No. 12/207,984 the Non-Final rejection dated Aug. 22, 2013.
In re the U.S. Appl. No. 12/207,984 the Final rejection dated Dec. 4, 2013.
International Preliminary Report on Patentability for International Application No. PCT/US2005/024042 dated Jan. 16, 2007.

(56) References Cited

OTHER PUBLICATIONS

International Search Report for International Application No. PCT/US2005/024042 dated May 12, 2006.
International Search Report for International Application No. PCT/US2005/004948 dated Jun. 9, 2009.
International Search Report re: PCT/US2015/051919 dated Apr. 14, 2016.
International Search Report re: PCT/US2017/052394 dated Nov. 21, 2017.
International Search Report re: PCT/US2017/052383 dated Dec. 6, 2017.
International Search Report re PCT/US2018/022842 dated Jun. 20, 2018.
International Search Report re PCT/US2018/022834 dated Jun. 22, 2018.
International Search Report re PCT/US2018/027790 dated Jun. 26, 2018.
Office action received from USPTO for co-pending U.S. Appl. No. 10/887,884 dated Apr. 25, 2006.
Office action received from USPTO for co-pending U.S. Appl. No. 10/779,721 dated Aug. 21, 2006.
Office action received from USPTO for co-pending U.S. Appl. No. 10/887,884 dated Oct. 12, 2006.
Office action received from USPTO for co-pending U.S. Appl. No. 10/779,721 dated Jan. 9, 2007.
Office Communication received from USPTO for co-pending U.S. Appl. No. 10/887,884 dated Jan. 22, 2007.
Office Action received from USPTO for co-pending U.S. Appl. No. 10/887,884 dated Feb. 1, 2007.
Office Action received from the USPTO for co-pending U.S. Appl. No. 12/163,021.
Office action received from USPTO for co-pending U.S. Appl. No. 10/779,721 dated Jul. 27, 2007.
Office Action received from USPTO for co-pending U.S. Appl. No. 10/887,884 dated Oct. 16, 2007.
Office Action received from USPTO for co-pending U.S. Appl. No. 10/887,884 dated Mar. 6, 2008.
Office action received from USPTO for co-pending U.S. Appl. No. 10/779,721 dated May 19, 2008.
Office action received from USPTO for co-pending U.S. Appl. No. 12/163,021 dated Jan. 9, 2010.
Office action received from USPTO for co-pending U.S. Appl. No. 12/163,021 dated Sep. 1, 2010.
Office action received from USPTO for co-pending U.S. Appl. No. 12/207,984 dated Sep. 1, 2010.
Office action received from USPTO for co-pending U.S. Appl. No. 12/163,021 dated Dec. 9, 2010.
Office action received from USPTO for co-pending U.S. Appl. No. 12/207,984 dated Dec. 9, 2010.
Office action received from USPTO for co-pending U.S. Appl. No. 12/163,021 dated May 13, 2011.
Office action received from USPTO for co-pending U.S. Appl. No. 12/163,021 dated Jul. 18, 2011.
Office action received from USPTO for co-pending U.S. Appl. No. 12/207,984 dated Aug. 1, 2011.
Office action received from USPTO for co-pending U.S. Appl. No. 12/163,021 dated Jan. 10, 2012.
Office action received from USPTO for co-pending U.S. Appl. No. 12/207,984 dated Jan. 17, 2012.
Office action received from USPTO for co-pending U.S. Appl. No. 12/207,984 dated Apr. 26, 2012.
Office action received from USPTO for co-pending U.S. Appl. No. 12/163,021 dated May 1, 2012.
Office action received from USPTO for co-pending U.S. Appl. No. 12/163,021 dated Sep. 17, 2012.
Office action received from USPTO for co-pending U.S. Appl. No. 12/207,984 dated Sep. 25, 2012.
Office action received from USPTO for co-pending U.S. Appl. No. 12/163,021 dated Aug. 14, 2013.
Office action received from USPTO for co-pending U.S. Appl. No. 12/207,984 dated Aug. 22, 2013.
Office action received from USPTO for co-pending U.S. Appl. No. 12/207,984 dated Dec. 4, 2013.
Office action received from USPTO for co-pending U.S. Appl. No. 12/163,021 dated Jan. 3, 2014.
Supplementary European Search Report for Application No. EP05769387 dated Jul. 9, 2009.
Supplementary European Search Report for Application No. EP05723162 dated Nov. 5, 2009.
Supplementary European Search Report for Application No. EP14166813 dated Jun. 30, 2014.
U.S. Appl. No. 09/430,177, filed Oct. 29, 1999.
U.S. Appl. No. 09/430,289, filed Oct. 29, 1999.
U.S. Appl. No. 09/430,180, filed Oct. 29, 1999.
U.S. Appl. No. 09/385,030, filed Aug. 30, 1999.
U.S. Appl. No. 09/176,889, filed Oct. 22, 1998.
U.S. Appl. No. 09/919,877, filed Aug. 2, 2001.
U.S. Appl. No. 10/779,721, filed Feb. 18, 2004.
Written Opinion re: PCT/US2015/051919 dated Apr. 14, 2016.
Written Opinion re: PCT/US2017/052394 dated Nov. 21, 2017.
Written Opinion re: PCT/US2017/052383 dated Dec. 6, 2017.
Written Opinion re: PCT/US2018/022842 dated Jun. 20, 2018.
Written Opinion re: PCT/US2018/027790 dated Jun. 26, 2018.
Written Opinion re PCT/US2018/022834 dated Jun. 22, 2018.
TissuGlu® Surgical Adhesive Patient Information Brochure (2014) Cohera Medical, Inc. 6 pages.
TissuGlu® Surgical Adhesive FDA Summary of Safety and Effectiveness Data (2014) Cohera Medical, Inc. 40 pages.
Wang et al 'Biodegradable microfluidic scaffolds for tissue engineering from amino alcohol-based poly(ester amide) elastomers' Organogenesis (2010) 6:4, pp. 212-216.
JP 7040744, 1995, English claims.
JP 3059327, 1991, English claims.
Japanese Office Action dated Feb. 19, 2019 for Design Appln. No. 2018-017274.
Japanese Office Action dated Feb. 26, 2019 for Patent Appln. No. 515463.
Office action received from USPTO for U.S. Appl. No. 15/964,538 dated Oct. 25, 2018.
Office action received from USPTO for U.S. Appl. No. 15/964,538 dated Dec. 27, 2018.
Office action received from USPTO for U.S. Appl. No. 15/490,176 dated Feb. 4, 2019.
Office action received from USPTO for U.S. Appl. No. 15/452,126 dated Nov. 16, 2018.
Office action received from USPTO for U.S. Appl. No. 14/864,033 dated Nov. 26, 2018.
Office action received from USPTO for U.S. Appl. No. 15/467,239 dated Feb. 28, 2019.
Office action received from USPTO for U.S. Appl. No. 15/675,159 dated May 14, 2019.

* cited by examiner

SCAFFOLDS WITH CHANNELS FOR JOINING LAYERS OF TISSUE AT DISCRETE POINTS

The present disclosure relates to resorbable scaffolds comprising channels that provide discrete fixation points of two layers of tissue to each other with an adhesive, while simultaneously enabling direct contact between layers of tissue being joined.

BACKGROUND

A number of methods exist for joining layers of tissue or closing wounds during surgery, such as for instance during abdominoplasty, whereby the tissues are joined utilizing surgical adhesives instead of suturing or stapling, whereby a layer of surgical adhesive is "sandwiched" between two layers of tissue. One known method of applying surgical adhesives is related to dispensing liquid adhesive on one layer of tissue from a dispenser, and then applying the second layer of tissue on top.

Problems with the known methods of tissue joining relate to (i) lack of uniform dispensing of liquid adhesive between layers of tissue being joined, resulting in variability of thickness of adhesive and (ii) complete separation of layers of tissue being joined by adhesives resulting in slower healing and potentially necrosis.

PCT publication No. WO2008082444 titled "ARTICLES AND METHODS FOR TISSUE REPAIR" discloses a method of medically treating a tissue comprising: directing a transfer device to a tissue surface, the transfer device having associated therewith a patterned array of an adhesive; transferring at least a portion of the patterned array of adhesive from the transfer device to the tissue surface by contact adhesion; moving the transfer device away from the tissue surface; positioning an article to be adhered adjacent at least a portion of the adhesive; and adhering the article to the tissue surface using the adhesive.

An article titled "Biodegradable microfluidic scaffolds for tissue engineering from amino alcohol-based poly(ester amide) elastomers" by Wang et al., Organogenesis 6:4, pp. 212-216; 2010, discloses fabrication of microfluidic networks from poly(ester amide), poly(1,3-diamino-2-hydroxypropane-co-polyol sebacate). The device is fabricated using a modified replica-molding technique, which is rapid, inexpensive, reproducible and scalable, making the approach ideal for both rapid prototyping and manufacturing of tissue engineering scaffolds.

U.S. Pat. No. 7,371,400 entitled "Multilayer device for tissue engineering" discloses a multilayer device for use in tissue engineering, comprising: (a) at least a first layer comprised of a polymer scaffold having a pattern of microchannels therein and (i) wherein the microchannels are suitable for the attachment and culturing of animal cells within the microchannels, and (ii) wherein the microchannels are connected for the circulation of fluid through the first layer, and (b) at least a second layer comprised of a polymer scaffold, wherein the first and second layers are joined or fastened together and the first layer is formed by forming a mold from a substrate material using a photoresist processing technique that includes: i) coating the substrate material with a photoresist; and ii) forming a pattern in the photoresist, and casting the first layer on the respective mold.

U.S. Pat. No. 8,353,966 entitled "Scaffold for bone and tissue repair in mammals" discloses a tissue scaffold for repair and regeneration of bone hard tissue or muscle, skin, or organ soft tissue, the scaffold comprising: a rigid scaffold body having a scaffold central axis, a scaffold transverse dimension, and a scaffold lengthwise dimension which is greater than the scaffold transverse dimension, the scaffold body having a compressive strength between about 20 and about 250 MPa and comprising: biocompatible inorganic glass fibers each having a fiber transverse dimension and a fiber lengthwise dimension which is at least about 10 times the fiber transverse dimension; and an interconnected porosity constituting between about 10 vol. % and about 35 vol. % of the scaffold body; wherein each of the fibers has a diameter between about 20 and about 5000 microns; wherein at least about 75 vol % of the fibers are longitudinally co-aligned and lie generally lengthwise of the scaffold central axis, are generally free of helical orientation about the scaffold central axis, and are arranged to define open channels within the scaffold which allow fluid flow into and lengthwise within the scaffold; and wherein the fibers are self-bonded together in that adjacent longitudinally aligned fibers are fused together.

U.S. Pat. No. 6,652,559 entitled "Wound closure system" discloses a wound closure system for closing a wound on a patient, comprising: an elongated flexible backing strip having opposite ends, first and second surfaces facing away from one another and a length and width sufficient to secure facing edges of the wound in close juxtaposition to one another, said backing strip comprising a first portion disposed between said ends and adapted to overlie the facing edges of said wound, and second and third portions disposed on either side of said first portion and each provided with a predetermined number of spaced-apart perforations extending through said backing strip from said first surface to said second surface, said first portion being free of any aperture extending through said backing strip from said first surface to said second surface; a first pressure-sensitive adhesive coated on at least part of the first surface of said backing strip including said second and third portions thereof, to adhere at least said second and third portions of said backing strip to the patient with the facing edges of said wound in said close juxtaposition; a first protective member removably attached to said backing strip and covering said pressure-sensitive adhesive; and a flowable, moisture-curable surgical adhesive for application into said perforations to strengthen the adhesion of said second and third portions of said backing strip to the patient; whereby after (a) removal of said protective member to expose said pressure-sensitive adhesive, (b) application of said backing strip with the exposed pressure-sensitive adhesive onto said patient to secure the facing edges of said wound in said close juxtaposition, and (c) application of said surgical adhesive into said apertures, said surgical adhesive flows through said perforations and upon curing forms discrete bonding sites cooperating with said backing strip to maintain the facing edges of said wound in said close juxtaposition without the cured adhesive adversely affecting the flexibility of said backing strip, wherein a second protective member having a second pressure-sensitive adhesive coated on one side thereof is removably attached to said backing strip and covers said second surface, said strip being disposed between said first and second protective members, and wherein said second protective member is provided with a corresponding number of perforations registering with the perforations defined in said second and third portions of said backing strip, and being in flow communication therewith.

U.S. Patent Application Publication No. 20130012988 entitled "Wound Closure Material" discloses wound closure material with a core of biodegradable material, wherein at least one side of the core of biodegradable material is provided with a multitude of discrete spots of an adhesive and the core of biodegradable material comprises an open cell structure.

U.S. Pat. No. 8,642,831 entitled "Device for promotion of hemostasis and/or wound healing" discloses a hemostatic matrix material comprising a surface and a plurality of open and interconnected cells, said matrix material comprising gelatine or collagen, wherein the surface of said matrix comprises at least one pharmaceutical composition printed onto said surface in individual and discrete locations, wherein said pharmaceutical composition comprises one or more hemostatic agents.

Synthetic tissue adhesive TissuGlu® Surgical Adhesive by Cohera Medical, Inc. is based on a polyurethane prepolymer and is applied in a spot-like discrete application of the adhesive during abdominoplasty, using a multi-point dispenser.

There continues to be a need for improved devices, systems, and methods for joining layers of tissue at discrete points enabling tissue layers being joined to establish contact between each other. There is a need in improved joining of tissues with adhesives, particularly improved devices and methods of delivering the adhesive in a layer with a uniform thickness. Additionally, there is a need in methods and devices which will provide faster tissue healing and joining and preventing tissue necrosis in the areas immediately adjacent the adhesive joint.

SUMMARY OF THE INVENTION

In one embodiment, a scaffold for joining two layers of tissue, comprises a substantially flat and flexible body having a top surface, a bottom surface and sidewalls; at least one channel within the body, the channel in fluid communication with an injection port;
a plurality of first passages on the top surface and a plurality of second passages on the bottom surface, said pluralities of first and second passages in fluid communication with the channel; and
a plurality of third passages penetrating the body from the top surface to the bottom surface, said plurality of third passages not in fluid communication with the channel.

According to another embodiment, there is provided a kit, comprising the scaffold for joining two layers of tissue, a syringe containing a polymerizable or cross-linkable fluid adhesive, and a cannula configured to connect the syringe with the injection port.

According to yet another embodiment, there is provided a method of adhesively joining layers of tissue the scaffold for joining two layers of tissue, comprising the steps of:
a) positioning the scaffold between the two layers of tissue;
b) connecting a pump containing a fluid cross-linkable or polymerizable adhesive to the body;
c) expressing the adhesive from the pump, advancing the adhesive into the injection port and into the channel;
d) further advancing the adhesive though the channel and into the pluralities of first and second passages and establishing contact of the adhesive with the layers of tissue;
e) polymerizing and/or cross-linking the adhesive in contact with the tissue, thus bonding the tissue layers to each other through the scaffold at discrete points of bonding corresponding to the pluralities of first and second passages;

f) establishing direct contact between the layers of tissue through the plurality of third passages spatially separate from the pluralities of first and second passages; and
g) disconnecting the pump from the scaffold.

DETAILED DESCRIPTION

Briefly, according to the embodiments of the present invention, absorbable or soluble scaffolds are configured for positioning between two layers of tissue being joined together. A liquid adhesive is then injected into the channels within the scaffolds. The liquid adhesive establishes discrete bonding spots to both layers of tissue being joined through pluralities of first and second passages on both sides of the scaffold. A plurality of third passages in the scaffold positioned between adhesively bonded areas enabling contact between both layers of tissue being joined.

Figure 1:
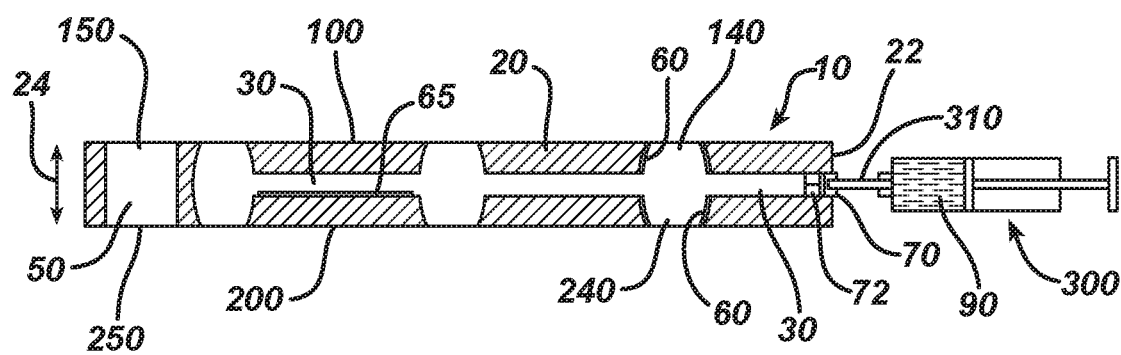
FIG. 1 shows an embodiment of the scaffold in a schematic side cross-sectional view.
Figure 2:
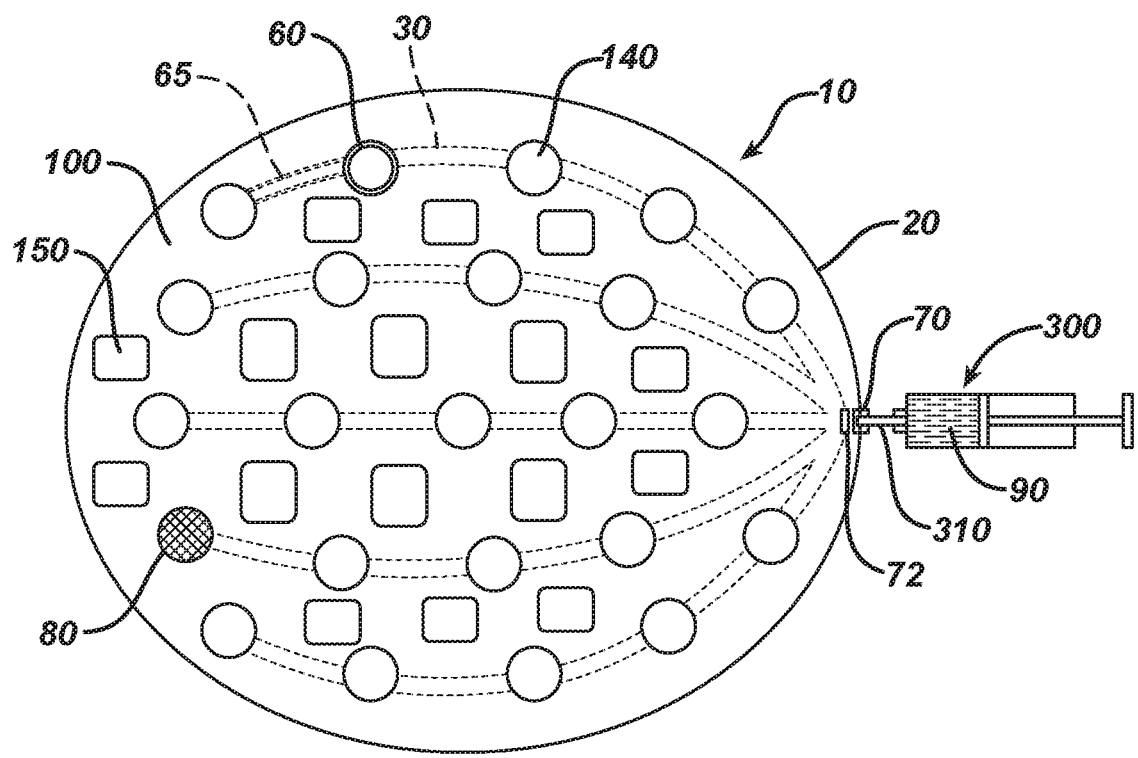
FIG. 2 shows an embodiment of the scaffold in a schematic top view.
Figure 3:
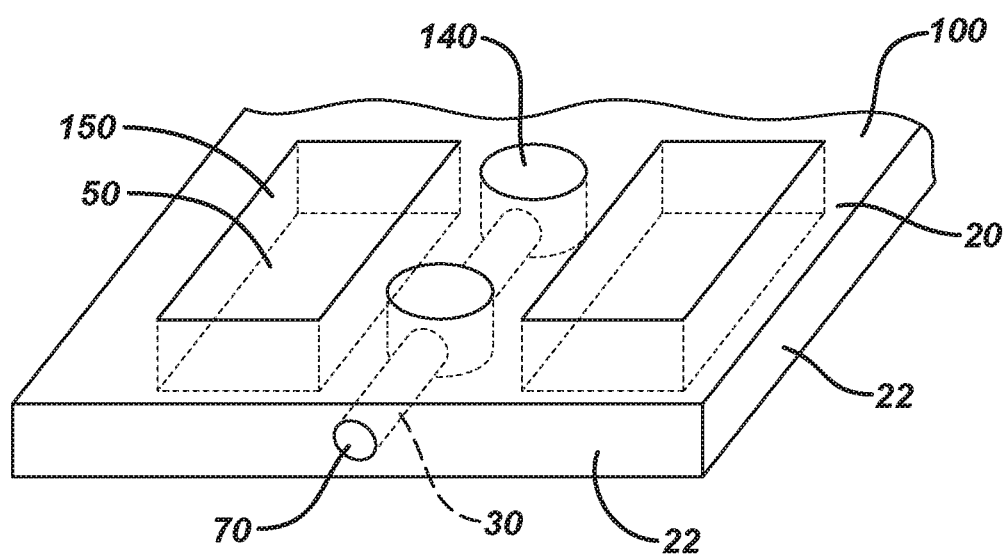
FIG. 3 shows a schematic perspective view of a portion of an embodiment of the scaffold.

Referring now to FIGS. 1 through 3, an embodiment of the scaffold 10 of the present invention is shown. FIG. 1 is showing a schematic side cross-sectional view; FIG. 2 is showing a schematic top view of scaffold 10; FIG. 3 is showing a schematic perspective view of a portion of scaffold 10.

Scaffold 10 comprises thin, flat, flexible body 20 made of resorbable or non-resorbable material. In a preferred embodiment, scaffold 10 body 20 is made of at least partially resorbable or at least partially soluble polymeric or composite material. In the most preferred embodiment, body 20 is fully resorbable or fully soluble. Body 20 is substantially flat and flexible and is defined by upper surface 100, lower surface 200 and side walls 22. Channel or multiple channels 30 are formed inside body 20 and are traversing body 20 generally parallel to upper surface 100 and lower surface 200, forming microfluidic pathways inside body 20. Channels 30 are starting at a single position at an entrance port 70 which is preferably positioned on side wall 22, but generally can be positioned anywhere on body 20. Channels 30 are terminating inside body 20 in the embodiment of FIGS. 1-3.

An optional one way valve 72 is installed inside entrance port 70, or inside channel 30 in the immediate proximity to entrance port 70, with valve 72 allowing fluid movement from port 70 into channels 30 (valve open in the direction from port 70 to channels 30) and preventing fluid movement from channels 30 back towards port 70 (valve closed in the direction from channels 30 to port 70).

Port 70 is configured for releasably accepting cannula 310 of adhesive expressing device 300, which comprises any source of flowable, fluid adhesive 90 which can be delivered under pressure into cannula 310. Device 300 can be a pump of any type. In a preferred embodiment, device 300 comprises a syringe filled with adhesive 90. Cannula 310 is designed for a snug but releasable fit into port 70.

Channels 30 are connected to a plurality of first passages 140 on upper surface 100 and to a plurality of second passages 240 on lower surface 200. Thus port 70 is in fluid communication with plurality of first passages 140 and plurality of second passages 240 via channels 30. Plurality of first passages 140 and plurality of second passages 240 comprise openings or exits from channels 30 to upper surface 100 and lower surface 200.

A plurality of third passages 50 comprises apertures or openings cut all the way through thickness 24 of body 20 in the areas of body 20 where no channels 30 and no pluralities of first and second passages 140, 240 are present. In one embodiment, plurality of third passages 50 are generally orthogonal to upper surface 100 and lower surface 200. Plurality of third passages 50 are traversing body 20 from upper surface 100 where plurality of third passages 50 are visible as upper entrances 150 to lower surface 200 where plurality of third passages 50 are visible as lower entrances 250. Plurality of third passages 50 are not in fluid communication with port 70, plurality of first passages 140, plurality of second passages 240, or channels 30. From 10% to 90% of upper surface 100 and lower surface 200 is covered by plurality of third passages 50, such as 20, 30, 40, 50, 60, 70, 80%. In a preferred embodiment, plurality of third passages 50 are empty apertures. Optionally, plurality of third passages 50 can be filled by rapidly soluble plugs (not shown), optionally containing medically useful agents, such as wound healing agents, fluid absorbent materials, etc.

In one embodiment, initiators and/or accelerators of adhesive polymerization or cross-linking can be disposed in channels 30 as shown by reference numeral 65, such as by being coated on channel 30 walls. More preferably, initiators or accelerators of adhesive polymerization or cross-linking can be disposed in pluralities of first and second passages 140, 240, as shown by reference numeral 60, such as by being coated on pluralities of first and second passages 140, 240 walls.

Figure 4:
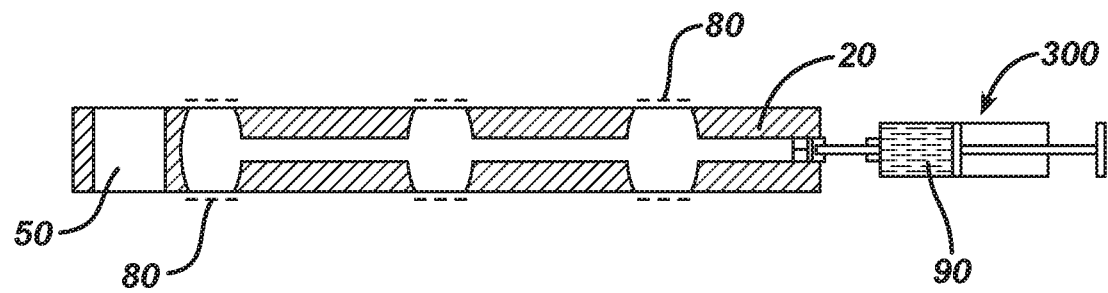
FIG. 4 shows an embodiment of the scaffold in a schematic side cross-sectional view.

In an alternative embodiment, mesh 80, coated with initiators and/or accelerators of adhesive polymerization or cross-linking is provided on upper surface 100 and lower surface 200 covering pluralities of first and second passages 140, 240 as shown in FIGS. 2, 4 in top view and schematic cross-sectional side view respectively.

Figure 5:
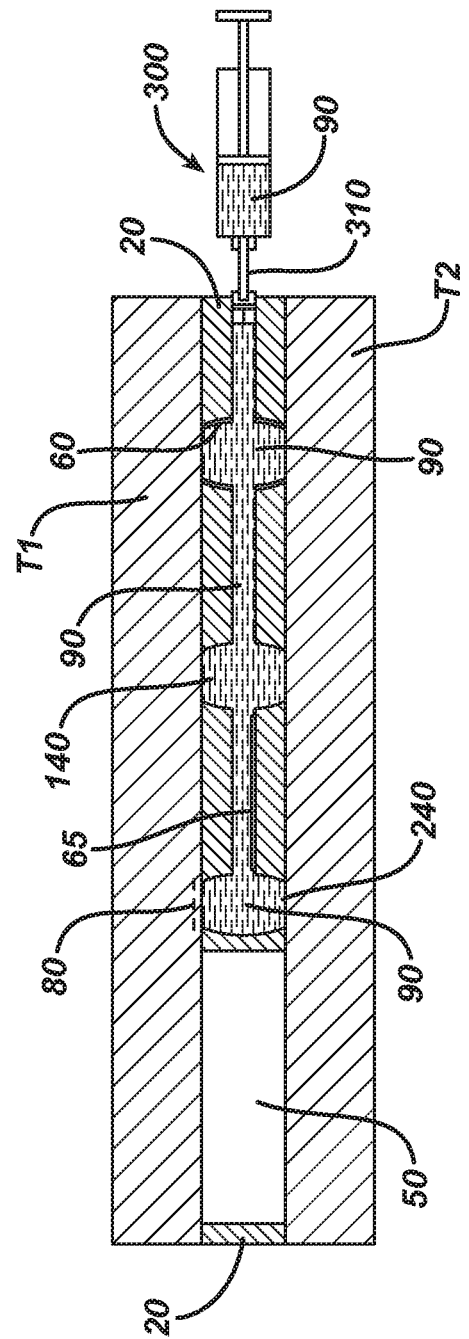
FIG. 5 shows an embodiment of the scaffold in a schematic side cross-sectional view.

In operation, and referring now to FIG. 5 showing a schematic cross-sectional side view, body 20 is positioned between two layers of tissue T1 and T2 which are being adhesively joined, with tissue T1 adjacent to and in contact with upper surface 100; with tissue T2 adjacent to and in contact with lower surface 200. In operation, the connection of scaffold 10 body 20 to cannula 310 is established prior to or after positioning of body 20 between tissues T1 and T2. Cross-linkable or polymerizable adhesive 90 is then expressed from pump 300. Adhesive 90 is advancing from pump 300 via cannula 310 into port 70, through optional one way valve 72, into channel or channels 30. As adhesive 90 is advancing though channels 30, adhesive 90 reaches plurality of first passages 140 and plurality of second passages 240 and gets into contact with tissue T1 on upper surface 100 and with tissue T2 on lower surface 200.

In one embodiment, adhesive 90 is polymerized or is cross-linking upon contact with tissues T1 and T2. In a more preferred embodiment, adhesive 90 is polymerized or is cross-linking after coming in contact with initiators and/or accelerators of adhesive polymerization and/or cross-linking.

Such initiators and/or accelerators can be coated or disposed non-releasably, i.e. immobilized in or on the body 20 while retaining activity to initiate or accelerate polymerization and/or cross-linking. In one embodiment, initiators and/or accelerators are disposed releasably, i.e. they can be at least partially released into and mix with flowing adhesive 90.

In a preferred embodiment, adhesive 90 is polymerized or is cross-linking after coming in contact with initiators and/or accelerators 65 releasably disposed in channel 30, or more preferably with initiators and/or accelerators 60 releasably disposed in pluralities of first and second passages 140, 240, or alternatively with initiators and/or accelerators releasably disposed on mesh 80. In one embodiment, adhesive 90 is polymerized or is cross-linking after coming in contact with initiators and/or accelerators releasably coated on mesh 80.

Rapid polymerization and/or crosslinking of adhesive 90 in contact with tissues T1 and T2 results in bonding of tissues T1 and T2 to each other through scaffold 10 at discrete points of bonding corresponding to pluralities of first and second passages 140, 240. After delivery of adhesive 90 into scaffold 10, cannula 310 is disconnected from scaffold 10.

Advantageously, areas of tissues T1 and T2 where no bonding has occurred can contact each other and establish healing contact through plurality of third passages 50 with tissue T1 contacting from upper surface 100 through upper entrances 150 and tissue T2 contacting from lower surface 200 through lower entrances 250. In FIGS. 3 and 5, plurality of third passages 50 are shown much larger than in FIGS. 1, 2, 4 to emphasize that plurality of third passages 50 can take as much space as available between and around pluralities of first and second passages 140, 240 and channels 30 to facilitate advantageous contact between tissues T1 and T2 through plurality of third passages 50.

Beneficially, scaffold 10 positioned between layers of tissue T1 and T2 enables uniform distribution of liquid adhesive for joining the layers of tissue together at discrete fixation points and not over the whole areas of exposed tissues, enabling tissue to tissue contact.

Eventually scaffold 10 resorbs or dissolves, leaving discrete adhesive connections between layers of tissue.

Figure 6:
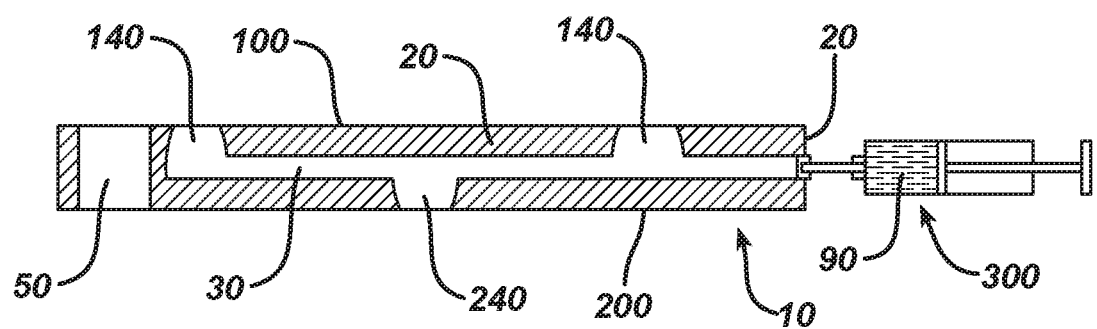
FIG. 6 shows an embodiment of the scaffold in a schematic side cross-sectional view.

Referring now to FIG. 6 showing a schematic side cross-sectional view of an alternative embodiment of scaffold 10, pluralities of first and second passages 140, 240 in this embodiment are offset from each other, i.e. at least some of plurality of first passages 140 on upper surface 100 are not directly opposite to or in registration with plurality of second passages 240 on lower surface 200.

Figure 7:
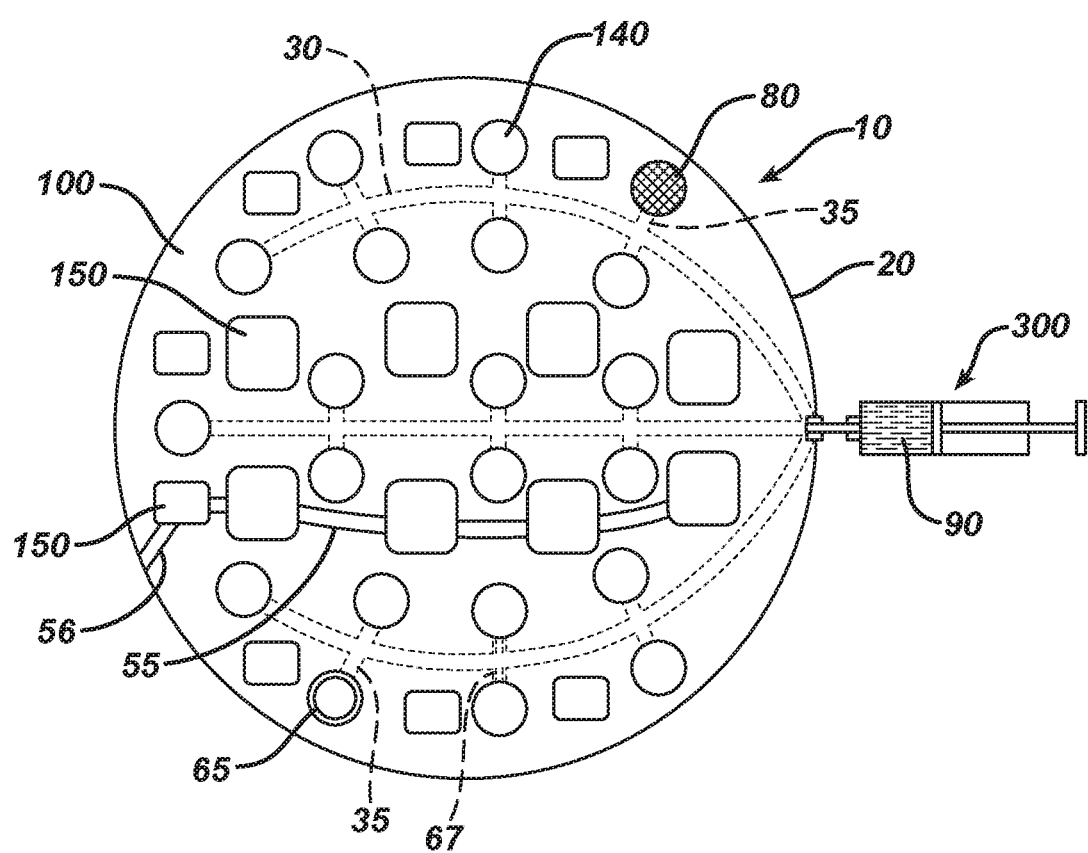
FIG. 7 shows an embodiment of the scaffold in a schematic top view.

Referring now to FIG. 7 showing a schematic top view of an alternative embodiment of scaffold 10, pluralities of first and second passages 140, 240 are connected to channels 30 through branched sub-channels 35. As shown initiators and/or accelerators 67 are releasably disposed in branched sub-channels 35, such as by being coated on sub-channel 35 walls. Alternatively, initiators and/or accelerators 65 are releasably disposed in pluralities of first and second passages 140, 240. Optionally, initiators and/or accelerators 67 and 65 are releasably disposed in both branched sub-channels 35 and in pluralities of first and second passages 140, 240 respectively.

Advantageously, in the embodiment of FIG. 7, cross-linking or polymerizing of adhesive 90 is initiated once adhesive 90 advanced into branched sub-channels 35 or in pluralities of first and second passages 140, 240. Due to pluralities of first and second passages 140, 240 being farther removed from channels 30 by the branched sub-channels 35 connecting pluralities of first and second passages 140, 240 to channels 30, there is a lesser possibility of adhesive 90 cross-linking or polymerizing in channels 30 prior to advancing to pluralities of first and second passages 140, 240 and thus blocking further advancement of adhesive 90 within channels 30.

Figure 8:
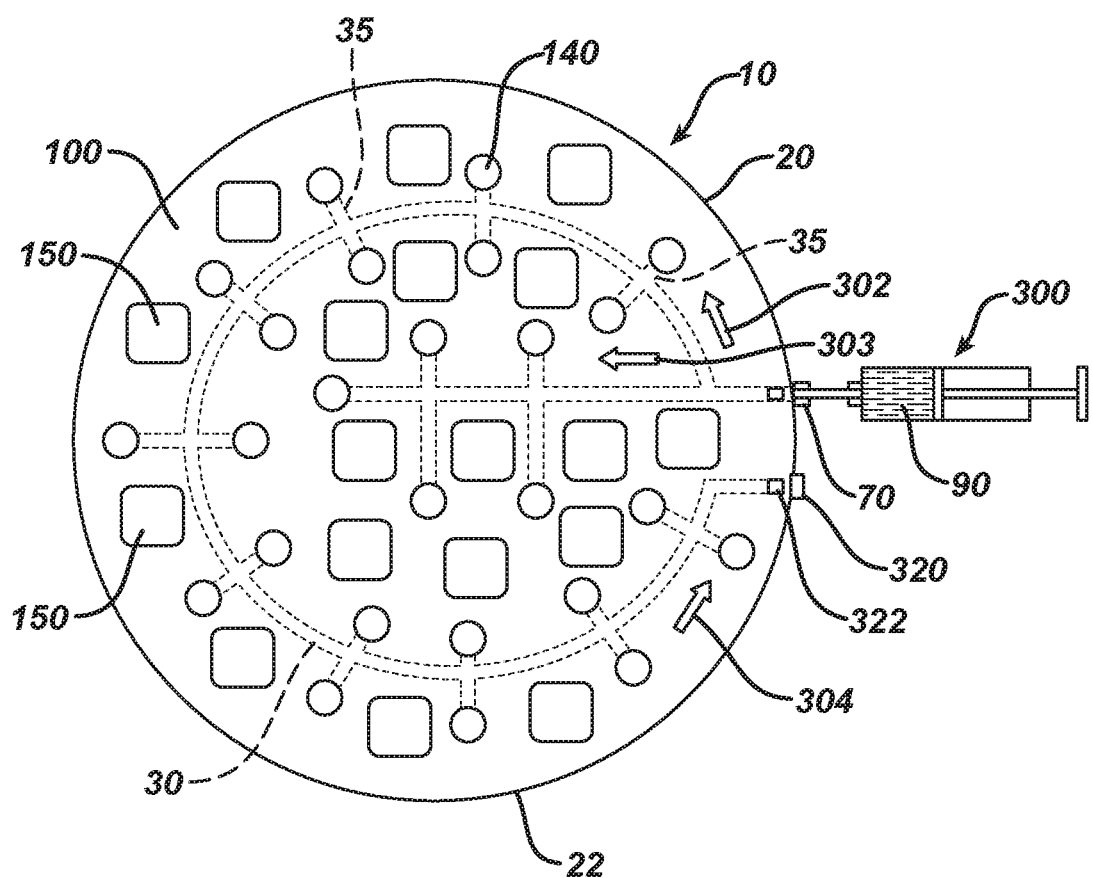
FIG. 8 shows an embodiment of the scaffold in a schematic top view.

Referring to FIG. 8, showing a schematic top view of an alternative embodiment of scaffold 10, in one embodiment, at least one channel 30 has an exit port 320 on side wall 22, with an optional one way valve 322 installed in channel 30 proximal to or within exit port 320 and open to fluid moving from channel 30 towards exit port 320 and out scaffold 10 body 20. As shown by arrow 302 adhesive 90 advances from port 70 and through one of channels 30 and towards exit port 320 as further shown by arrow 304. Arrow 303 shows advancement of adhesive 90 in another channel 30 which optionally does not terminate at exit port 320 on side wall 22 but terminates inside body 20.

Figure 9:
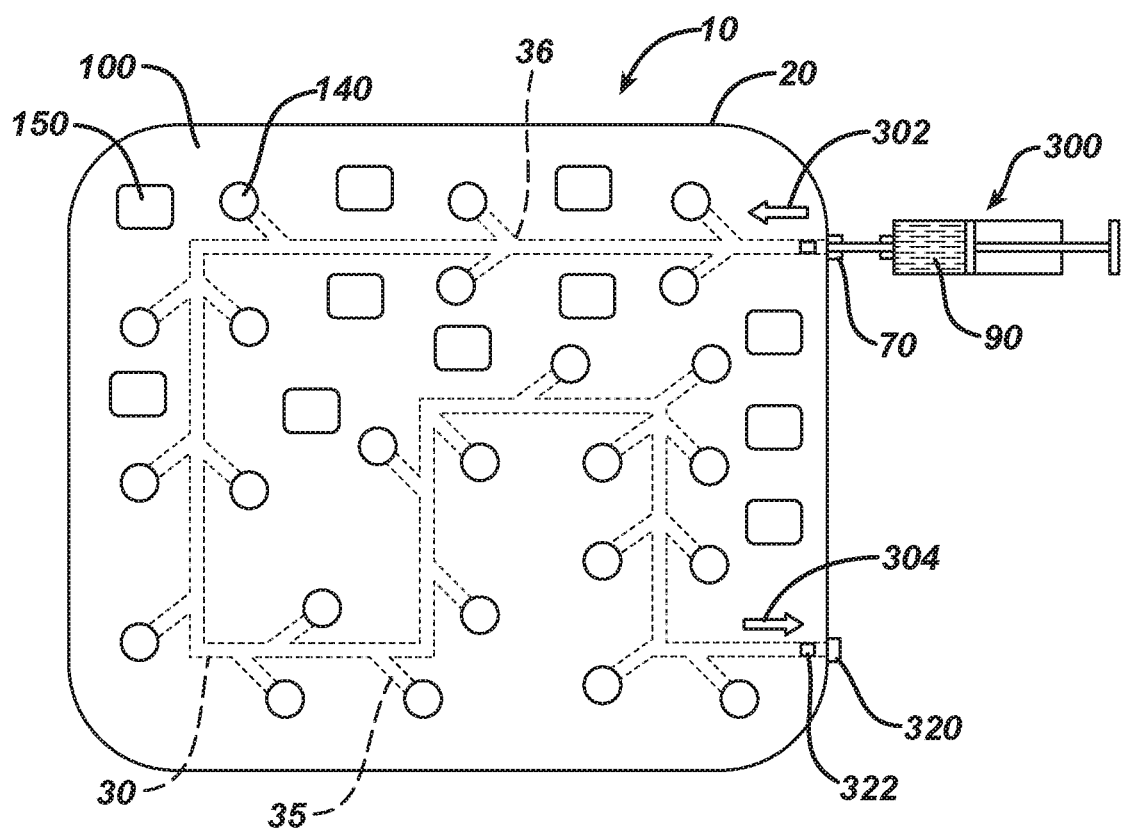
FIG. 9 shows an embodiment of the scaffold in a schematic top view.

Referring to FIG. 9, showing a schematic top view of an alternative embodiment of scaffold 10, in this embodiment, there is only one channel 30 that passes through body 20 in a winding fashion covering a substantial portion of body 20, or most of body 20. Channel 30 has an exit port 320 on side wall 22, with an optional one way valve 322 installed in channel 30 proximal to or within exit port 320 and open to fluid moving from channel 30 towards exit port 320 and out of scaffold 10 body 20. As shown by arrow 302 adhesive 90 advances from port 70 and through one of channels 30 and towards exit port 320 as further shown by arrow 304.

In one embodiment, suction or vacuum is provided through exit port 320 to facilitate filling of channels 30.

Branched sub-channels 35 can be branching from channel 30 at any angle. FIGS. 7 and 8 show branched sub-channels 35 branching at about right angle from channel 30. FIG. 9 shows branched sub-channels 35 branching at a sharp angle from channel 30 with entrances 36 of branched sub-channels 35 being closer upstream to port 70 than pluralities of first and second passages 140 and 240 located at the end of branched sub-channels 35 to reduce the probability of backflow back into channel 35 of adhesive 90 that has already contacted crosslinking or polymerization accelerator or initiator in pluralities of first and second passages 140 and 240 and/or in branched sub-channels 35, such backflow potentially resulting in blockage.

Body 20 can be of any geometrical shape or form, such as square, rectangular, round, oval, triangular etc. FIGS. 1, 2, 7, 8 show substantially round shape of body 20. FIG. 9 shows substantially rectangular shape of body 20.

In one embodiment, there are provided surface grooves 55 connecting at least some of plurality of third passages 50 to each other as shown in FIG. 7. Optionally surface grooves 55 are running all the way to periphery of scaffold 10 body 20 as shown by reference numeral 56. Surface grooves 55 are cut into upper surface 100 and lower surface 200 and are not in fluid communication with channels 30, or with pluralities of first and second passages 140, 240. Surface grooves 55 are enabling bodily fluids movement or drainage from the area of joining tissues T1 and T2 with bodily fluids moving around discrete joining bonding points formed by adhesive 90.

Adhesive

Adhesive 90 can be any type of biocompatible and rapidly cross-linkable and/or polymerizable compound or mixture of compounds. Rapidly cross-linkable and/or polymerizable means that after initiators or accelerators are added, or after the adhesive is formed from two or more components, it is capable of curing, i.e. cross-linking and/or polymerizing within 0.2 min to about 20 min, more preferably within 0.5 min to 10 min, such as 1, 2, 3, 5 min.

In one embodiment, adhesive 90 is formed prior to injection into scaffold 10, for instance by mixing two components contained in separate barrels of a two-barrel syringe, e.g. by passing these two components through a mixing tip which is connected to port 70. In this embodiment, there is no crosslinking initiator or accelerator disposed inside of scaffold 10. In one embodiment, adhesive 90 is formed by mixing fibrinogen and thrombin together, then injecting the resulting mixture into port 70.

In one embodiment, adhesive 90 comprises fibrinogen, and crosslinking initiator or accelerator disposed inside of scaffold 10 comprises thrombin.

In a preferred embodiment, the polymerizable adhesive composition may comprise a polymerizable monomeric adhesive. In embodiments, the polymerizable adhesive composition comprises a polymerizable 1,1-disubstituted ethylene monomer formulation. In embodiments, the polymerizable adhesive composition comprises a cyanoacrylate formulation. In embodiments, synthetic polymerizable adhesive materials such as polyurethane, polyethylene glycol, acrylates, glutaraldehyde and biologically based adhesives may be used.

Suitable .alpha.-cyanoacrylate monomers which may be used, alone or in combination, include alkyl .alpha.-cyanoacrylates such as 2-octyl cyanoacrylate; dodecyl cyanoacrylate; 2-ethylhexyl cyanoacrylate; butyl cyanoacrylate such as n-butyl cyanoacrylate; ethyl cyanoacrylate; methyl cyanoacrylate or other .alpha.-cyanoacrylate monomers such as methoxyethyl cyanoacrylate; 2-ethoxyethyl cyanoacrylate; 3-methoxybutyl cyanoacrylate; 2-butoxyethyl cyanoacrylate; 2-isopropoxyethyl cyanoacrylate; and 1-methoxy-2-propyl cyanoacrylate. In embodiments, the monomers are ethyl, n-butyl, or 2-octyl .alpha.-cyanoacrylate. Other cyanoacrylate monomers which may be used include alkyl ester cyanoacrylates, such as those prepared by the Knoevenagel reaction of an alkyl cyanoacetate, or an alkyl ester cyanoacetate, with paraformaldehyde, subsequent thermal cracking of the resultant oligomer and distillation.

Many other adhesive formulations can be used and are known to a skilled artisan. For example, mixtures containing PEG Succinimidyl Glutarate can be used as a flowable adhesive.

Scaffold

Thickness 24 of body 20 (or height of sidewalls 22) is from about 0.2 mm to about 8 mm, more preferably from 1 mm to 6 mm, such as 1, 2, 3, 4 mm. The gross surface area of body 20 when measured from a top view, as for instance shown in FIGS. 2, 7-9, is from about 3 $cm^2$ to about 400 $cm^2$, more preferably from 5 $cm^2$ to 300 $cm^2$, such as 10, 20, 50, 100, 150, 200 $cm^2$. In some embodiments, when body 20 is substantially circular, the diameter of the circle is from about 2 cm to about 20 cm, such as 5 cm, 10 cm, 15 cm, 20 cm. In some embodiments, when body 20 is substantially square, the side of the square is from about 2 cm to about 20 cm, such as 3, 5, 10, 15, 20 cm.

Channels 30 can have circular or rectangular cross-section, or any other geometry. In circular cross-section, channels 30 have diameter from 0.3 mm to 3 mm, such as 0.5, 1, 2, 3 mm. In some embodiments, channels 30 are taking from 20 to 90% of the thickness of body 20.

Pluralities of first and second passages 140, 240, can be of any geometry, including circular, rectangular, etc. When circular, pluralities of first and second passages 140, 240 have diameters from about 1 mm to about 8 mm, such as 2, 3, 4, 5 mm. Plurality of third passages 50 can be of any geometry, including circular, rectangular, etc. In some embodiments, upper entrances 150 and lower entrances 250 take 50%-95% of space on upper 100 and lower 200 surfaces of body 20 which is not taken by pluralities of first and second passages 140, 240, with positioning of plurality of third passages 50 configured so as to not intersect any channels 30 and or sub-channels 35.

When circular, upper entrances 150 and lower entrances 250 can have diameters ranging from 3 mm to 30 mm, such as 5, 8, 10, 15, 20 mm.

The portion of total area of space on upper 100 and lower 200 surfaces of body 20 taken by pluralities of first and second passages 140, 240 can be from 5% to 50%; the portion of total area of space on upper 100 and lower 200 surfaces of body 20 taken by upper entrances 150 and lower entrances 250 can be from 50% to 95%.

Scaffolds 10 can be manufactured by many techniques known to a skilled artisan in the field of microfluidic devices, such as injection molding, layers bonding, machining, 3D printing, etc., and combinations thereof. In one method, channels and passages can be formed in separate layers of polymeric material and these layers can then be bonded thus forming enclosed channels.

Body 20 may be formed of either synthetic, semi-synthetic, or natural materials or combinations thereof. In particular, suitable materials include, for example, PLGA or poly(lactic-co-glycolic acid, polylactic acid, polyglycolic acid, polycaprolactone, nylon, polyolefin, polyethylene, polypropylene, ethylene propylene copolymers, and ethylene butylene copolymers, polyurethanes, polyurethane foams, polystyrenes, plasticized polyvinylchlorides, polyesters, polyamides, copolymers and mixtures of the above, cotton, collagen, gelatin, and composites of the above. Body 20 can be porous or non-porous.

Scaffold 10 may be either biodegradable, or not biodegradable, or partially biodegradable. By "biodegradable" it is meant that scaffold 10 biodegrades over time in vivo, such that it does not require physical removal after a set period of time. Thus, for example, a biodegradable material is one that, in the in vivo environment, will biodegrade over a period of from about one week to about five years. A non-biodegradable material is one that does not biodegrade in an in vivo environment within about five years.

Initiator

Scaffold 10 in some embodiments includes one or more chemical materials located in or on it. For example, one or more chemical substances may be dispersed in or on body 20, preferably within channels 30, pluralities of first and second passages 140, 240, sub-channels 35, on mesh 80, such as being chemically bound, physically bound, coated, absorbed, or adsorbed to it. Thus, for example, the scaffold 10 preferably includes at least a polymerization initiator or rate accelerator or modifier, and may optionally include one or more bioactive materials.

For example, a polymerization initiator or accelerator or rate modifier may be loaded in or on scaffold 10 so that the initiator or rate modifier provides the desired initiation or rate modification effect to a subsequently applied polymerizable adhesive composition. The polymerization initiator or rate modifier may be immobilized in or on body 20, so that the initiator or rate modifier does not become detached from body 20 and its residues are dispersed in the resultant polymeric material. Alternatively, for example, the polymerization initiator or rate modifier may be initially attached to body 20, but only in such a manner that it becomes mobilized or solubilized by a subsequently applied polymerizable adhesive composition and dispersed in the resultant polymeric material.

If desired, a combination of chemical substances may also be provided in or on scaffold 10, to provide multiple effects. For example, a first chemical species (such as a polymerization initiator or rate modifier) may be immobilized in or on scaffold 10, while a second, different chemical species (such as a bioactive material) may be detachably attached to scaffold 10. Other combinations of chemical species and resultant effects are also envisioned.

The chemical substance may be applied in a uniform manner to scaffold 10, such that there is a substantially uniform concentration of the chemical substance within scaffold 10. Alternatively, the chemical substance may be applied such that a concentration gradient exists across or through scaffold 10.

When present in or on scaffold 10, the chemical substances (i.e., polymerization initiator, rate modifier, and/or bioactive materials, or other additives), may be incorporated in or on scaffold 10 in any suitable manner. For example, the chemical substance may be added to scaffold 10 by contacting scaffold 10 with a solution, mixture, or the like including the chemical substances. The chemical substance may be added to scaffold 10, for example, by dipping, spraying, roll coating, gravure coating, brushing, vapor deposition, or the like. Alternatively, the chemical substance may be incorporated into or onto scaffold 10 during manufacture of scaffold 10, such as during molding.

The polymerization initiator or rate modifier loaded in or on scaffold 10 may provide a number of advantages for example, so as to provide faster polymerization time. The concentration of polymerization initiator or rate modifier may be increased to provide even faster polymerization time.

Because the polymerization initiator or rate modifier is loaded directly in or on scaffold 10, it is not necessary to mix the polymerizable adhesive composition with a polymerization initiator or rate modifier prior to application. This may allow a longer working time, where the polymerizable monomer composition may be more precisely and carefully applied over a longer period of time.

Such suitable initiators are known in the art and are described, for example, in U.S. Pat. Nos. 5,928,611 and 6,620,846, both incorporated herein by reference in their entireties, and U.S. Patent Application No. 2002/0037310, also incorporated herein by reference in its entirety. Quaternary ammonium chloride and bromide salts useful as polymerization initiators are particularly suitable. By way of example, quaternary ammonium salts such as domiphen bromide, butyrylcholine chloride, benzalkonium bromide, acetyl choline chloride, among others, may be used.

Benzalkonium or benzyltrialkyl ammonium halides such as benzyltrialkyl ammonium chloride may be used. When used, the benzalkonium halide may be benzalkonium halide in its unpurified state, which comprises a mixture of varying chain-length compounds, or it can be any suitable purified compound including those having a chain length of from about 12 to about 18 carbon atoms, including but not limited to C12, C13, C14, C15, C16, C17, and C18 compounds. By way of example, the initiator may be a quaternary ammonium chloride salt such as benzyltrialkyl ammonium chloride (BTAC).

Other initiators or accelerators may also be selected by one of ordinary skill in the art without undue experimentation. Such suitable initiators or accelerators may include, but are not limited to, detergent compositions; surfactants: e.g., nonionic surfactants such as polysorbate 20 (e.g., Tween 20™ from ICI Americas), polysorbate 80 (e.g., Tween 80™ from ICI Americas) and poloxamers, cationic surfactants such as tetrabutylammonium bromide, anionic surfactants such as sodium tetradecyl sulfate, and amphoteric or zwitterionic surfactants such as dodecyldimethyl(3-sulfopropyl) ammonium hydroxide, inner salt; amines, imines and amides, such as imidazole, arginine and povidine; phosphines, phosphites and phosphonium salts, such as triphenylphosphine and triethyl phosphite; alcohols such as ethylene glycol, methyl gallate; tannins; inorganic bases and salts, such as sodium bisulfite, calcium sulfate and sodium silicate; sulfur compounds such as thiourea and polysulfides; polymeric cyclic ethers such as monensin, nonactin, crown ethers, calixarenes and polymeric-epoxides; cyclic and acyclic carbonates, such as diethyl carbonate; phase transfer catalysts such as Aliquat 336; organometallics such as cobalt naphthenate and manganese acetylacetonate; and radical initiators or accelerators and radicals, such as di-t-butyl peroxide and azobisisobutyronitrile.

Mixtures of two or more, such as three, four, or more, initiators or accelerators may be used. A combination of multiple initiators or accelerators may be beneficial, for example, to tailor the initiator of the polymerizable monomer species. For example, where a blend of monomers is used, a blend of initiators may provide superior results to a single initiator. For example, the blend of initiators can provide one initiator that preferentially initiates one monomer, and a second initiator that preferentially initiates the other monomer, or can provide initiation rates to help ensure that both monomer species are initiated at equivalent, or desired non-equivalent, rates. In this manner, a blend of initiators can help minimize the amount of initiator necessary. Furthermore, a blend of initiators may enhance the polymerization reaction kinetics.

It should be understood that the foregoing disclosure and description of the embodiments of the present invention are illustrative and explanatory thereof and various changes in the size, shape and materials as well as in the description of the preferred embodiment may be made without departing from the spirit of the invention.

What is claimed is:

1. A scaffold for joining two layers of tissue, comprising:
   a) a substantially flat and flexible body having a top surface, a bottom surface and sidewalls;
   b) at least one channel within the body, the channel in fluid communication with an injection port for flow of an adhesive;
   c) a plurality of discrete first passages penetrating the top surface and a plurality of discrete second passages penetrating the bottom surface, said pluralities of first and second passages in fluid communication with the channel; and
   d) a plurality of third passages comprising apertures penetrating the body from the top surface to the bottom surface, said plurality of third passages not in fluid communication with the channel,
   wherein said scaffold further comprising a one-way valve positioned within the channel proximal to the injection port, the one way valve open for flow of the adhesive into the channel from the injection port and closed for flow from the channel towards the injection port,
   wherein said scaffold is configured for positioning between and adhesively joining a first tissue and a second tissue with the adhesive with said top surface configured to be adjacent to and in contact with the first tissue and said bottom surface configured to be adjacent to and in contact with the second tissue; and
   wherein said third passages are configured for establishing direct contact between the first tissue and the second tissue.

2. The scaffold of claim 1, wherein said pluralities of first and second passages are in fluid communication with the channel through branched sub-channels.

3. The scaffold of claim 2, wherein an accelerator or an initiator of cross-linking or polymerization is disposed in or on the body.

4. The scaffold of claim 3, wherein the accelerator or the initiator comprises quaternary ammonium salt.

5. The scaffold of claim 3, wherein the accelerator or the initiator is disposed in the channel, in the pluralities of first and second passages, in the branched sub-channels, or in any combinations of the channel, the pluralities of first and second passages, and the branched sub-channels.

6. The scaffold of claim 3, wherein the pluralities of first and second passages are covered by a porous mesh, and wherein the accelerator or the initiator is disposed on the porous mesh.

7. The scaffold of claim 1, wherein the plurality of first passages on the top surface and the plurality of second passages on the bottom surface are not directly opposing each other.

8. The scaffold of claim 1, wherein the at least one channel terminates with an exit port, the scaffold further comprising an optional one way valve positioned within the channel proximal to the exit port, the one way valve open for flow from the channel towards the exit port and closed for flow from exit port towards the channel.

9. The scaffold of claim 1, further comprising a plurality of grooves in the top surface and in the bottom surface, the grooves connecting at least some of the plurality of third passages, wherein the grooves are not in fluid communication with the pluralities of first and second passages.

10. The scaffold of claim 1, wherein the body is biodegradable or soluble.

11. The scaffold of claim 1, wherein the plurality of third passages are at least partially filled with a rapidly soluble or rapidly absorbable biocompatible material.

12. The scaffold of claim 1, wherein the injection port is positioned on the sidewall.

13. A kit, comprising:
   a) a scaffold comprising:
      i. a substantially flat and flexible body having a top surface, a bottom surface and sidewalls;
      ii. at least one channel within the body, the channel in fluid communication with an injection port;
      iii. a plurality of discrete first passages penetrating the top surface and a plurality of discrete second passages penetrating the bottom surface, said pluralities of first and second passages in fluid communication with the channel; and
      iv. a plurality of third passages comprising apertures penetrating the body from the top surface to the bottom surface, said plurality of third passages not in fluid communication with the channel,
      wherein said scaffold further comprising a one-way valve positioned within the channel proximal to the injection port, the one way valve open for flow into the channel from the injection port and closed for flow from the channel towards the injection port, wherein said scaffold is configured for positioning between and adhesively joining a first tissue and a second tissue with said top surface configured to be adjacent to and in contact with the first tissue and said bottom surface configured to be adjacent to and in contact with the second tissue; and wherein said third passages are configured for establishing direct contact between the first tissue and the second tissue, b) a syringe containing a polymerizable or cross-linkable fluid adhesive, and c) a cannula configured to connect the syringe with the injection port.

14. A method of adhesively joining layers of tissue together using a scaffold comprising:
  i. a substantially flat and flexible body having a top surface, a bottom surface and sidewalls;
  ii. at least one channel within the body, the channel in fluid communication with an injection port;
  iii. a plurality of discrete first passages penetrating the top surface and a plurality of discrete second passages penetrating the bottom surface, said pluralities of first and second passages in fluid communication with the channel; and
  iv. a plurality of third passages comprising apertures penetrating the body from the top surface to the bottom surface, said plurality of third passages not in fluid communication with the channel, wherein said scaffold further comprising a one-way valve positioned within the channel proximal to the injection port, the one way valve open for flow into the channel from the injection port and closed for flow from the channel towards the injection port, wherein said scaffold is configured for positioning between and adhesively joining a first tissue and a second tissue with said top surface configured to be adjacent to and in contact with the first tissue and said bottom surface configured to be adjacent to and in contact with the second tissue; and wherein said third passages are configured for establishing direct contact between the first tissue and the second tissue, the method comprising the steps of:
a) positioning the scaffold between the two layers of tissue;
b) connecting a pump containing a fluid cross-linkable or polymerizable adhesive to the injection port;
c) expressing the adhesive from the pump, advancing the adhesive into the injection port and into the channel;
d) further advancing the adhesive though the channel and into the pluralities of first and second passages and establishing contact of the adhesive with the layers of tissue;
e) polymerizing and/or cross-linking the adhesive in contact with the tissue, thus bonding the tissue layers to each other through the scaffold at discrete points of bonding corresponding to the pluralities of first and second passages;
f) establishing direct contact between the layers of tissue through the plurality of third passages spatially separate from and not in fluid communication with the pluralities of first and second passages; and
g) disconnecting the pump from the injection port.

15. The method of claim 14, wherein the adhesive comprises cyanoacrylate monomers.

16. The method of claim 14, wherein the adhesive comprises fibrinogen.

17. The method of claim 14, wherein the adhesive comprises PEG Succinimidyl Glutarate.

18. The method of claim 14, further comprising the step of the adhesive reacting with an initiator or an accelerator disposed in or on the body.

* * * * *